United States Patent [19]

Sigwart

[11] Patent Number: 5,443,500
[45] Date of Patent: Aug. 22, 1995

[54] INTRAVASCULAR STENT

[75] Inventor: Ulrich Sigwart, Morges, Switzerland

[73] Assignee: Advanced Cardiovascular Systems, Inc., Santa Clara, Calif.

[21] Appl. No.: 225,421

[22] Filed: Apr. 8, 1994

Related U.S. Application Data

[63] Continuation of Ser. No. 958,460, Oct. 7, 1992, abandoned, which is a continuation of Ser. No. 464,401, Jan. 12, 1990, abandoned.

[30] Foreign Application Priority Data

Jan. 26, 1989 [CH] Switzerland .................. 237/89

[51] Int. Cl.$^6$ ............................................. A61F 2/06
[52] U.S. Cl. ................................... 623/1; 623/12; 606/192; 606/194; 606/195
[58] Field of Search ............... 623/1, 12, 192, 194, 623/195

[56] References Cited

U.S. PATENT DOCUMENTS

| | | | |
|---|---|---|---|
| 4,739,762 | 4/1988 | Palmaz | 623/1 |
| 4,740,207 | 4/1988 | Kreamer | 623/1 |
| 4,877,030 | 10/1989 | Beck et al. | 623/1 |
| 5,007,926 | 4/1991 | Derbyshire | 623/1 |
| 5,133,732 | 7/1992 | Wiktor . | |
| 5,135,536 | 8/1992 | Hillstead . | |
| 5,344,426 | 9/1994 | Lau et al. | 623/1 |

FOREIGN PATENT DOCUMENTS

| | | |
|---|---|---|
| WO83/00997 | 3/1983 | European Pat. Off. . |
| 0221570 | 5/1987 | European Pat. Off. . |
| 0246998 | 11/1987 | European Pat. Off. . |
| 3640745 | 6/1987 | Germany . |

Primary Examiner—Randall L. Green
Assistant Examiner—Bruce Snow
Attorney, Agent, or Firm—Fulwider Patton Lee & Utecht

[57] ABSTRACT

The intravascular stent intended for implantation in a stenotic area or zone of obstruction of a blood vessel consists of a flat sheet which is perforated to form a kind of a reticulated or lattice type structure with undeformable links and made of malleable material. Said sheet is temporarily rolled up and locked in a spiral with a relatively small diameter (d) on a deflated angioplasty balloon mounted on the end of a catheter and is held in said rolled-up state by a tie laced into overlapping links. Once the device is in place in the restricted area of the blood vessel to be treated and after tie is removed, the rolled sheet is expanded to a desired diameter (D) by inflating balloon and is then held in this expanded state by integrated holding flaps which, after the balloon is deflated, extend through the links and engage the edges thereof under the pressure of the vessel.

11 Claims, 1 Drawing Sheet

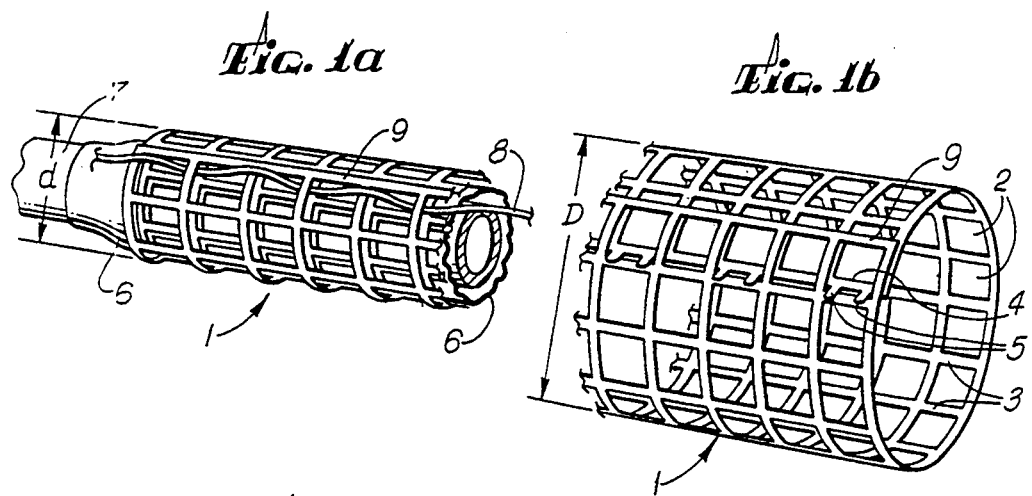
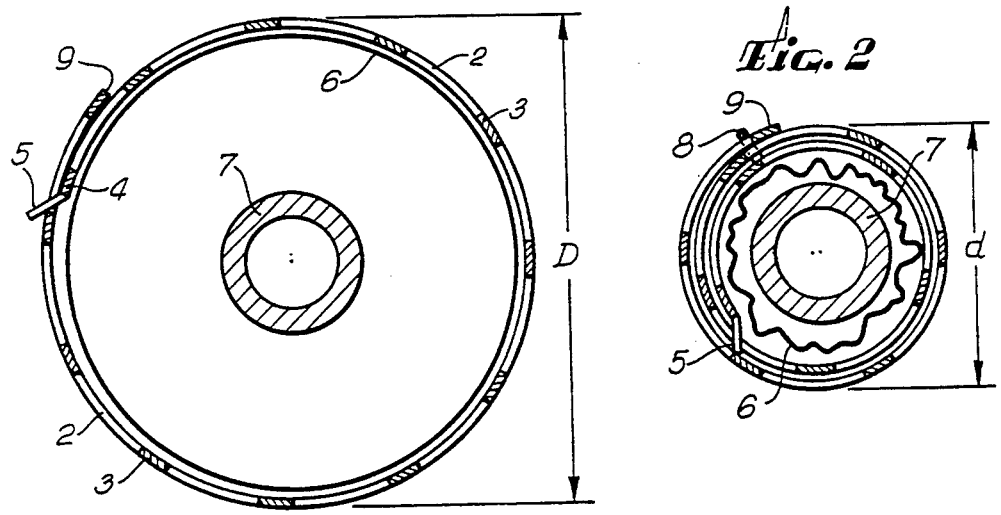
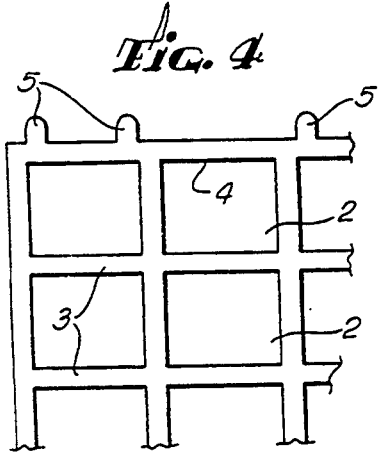
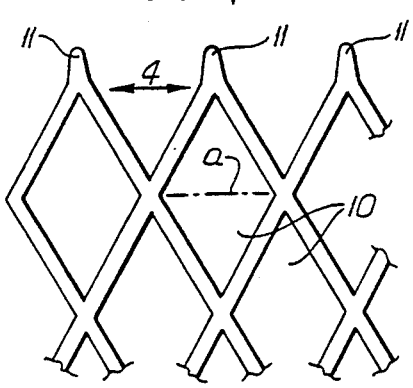

INTRAVASCULAR STENT

This application is a continuation of application Ser. No. 07/958,460, filed Oct. 7, 1992 now abandoned which is a continuation of Ser. No. 07/464,401 filed Jan 12, 1990, now abandoned.

BACKGROUND OF THE INVENTION

The present invention is directed to a cylindrically shaped, radially expandable intravascular endoprosthesis formed of biocompatible material. The device is intended to be transported and introduced into the area of stenosis or obstruction of a blood vessel by means of a catheter with a guidewire in a relatively tightly wound or rolled-up state. Means are provided to temporarily hold the endoprosthetic device or stent in a wound or rolled-up state around the catheter during transport and introduction into said area.

There are different kinds of intravascular endoprostheses, commonly called stents, which have the common characteristic of being presented into a patient's blood vessel or other body cavity or lumen in the shape of a cylindrical cuff, the wall of which forms a kind of lattice of deformable mesh in order to permit its diametrical expansion and contraction. In one of these types such as shown in U.S. Pat. No. 4,740,207 (Kreamer), the stent is made of stainless steel sheet and appears originally in a rolled-up form of smaller diameter. After being introduced into the area of the vessel to be treated, it is expanded by means of an angioplasty balloon on the distal end of a catheter which is disposed on the interior of the rolled-up stent. The balloon is inflated with a fluid to the desired diameter which usually corresponds to the maximum expansion of which said balloon is capable.

In another type, such as described in U.S. Pat. No. 3,868,956, and Japanese Application 57-89859 published Jun. 4, 1982, the stent is made of thermo-expandable material such as nitinol which is dilated by heat after being implanted.

Finally, in a recently developed type, the stent is made of stainless steel wires of good elastic quality which are interwoven into a mesh, the diameter of which is selected to be slightly larger than the normal inner diameter of the vessel to be treated, so that it can exert a residual radial pressure on the arterial wall after being implanted. Before being introduced into the patient's blood vessel and while advancing the stent into the area of the blood vessel to be treated, the stent is reduced in diameter by stretching longitudinally and kept compressed on the catheter by a withdrawable sleeve. Once the device is implanted, the progressive withdrawal of said membrane permits the deployment of the stent in the vascular lumen.

Of these three known kinds of stents, the second, the one made of thermo-expandable material, presents great inconvenience because it is difficult to manipulate and implant, and its expansion is hard to control and is not reliable.

The above inconvenience does not exist in the stents made of stainless steel wire, but they still present a defect in that their expansion to a desired maximum diameter takes place at the cost of a proportional shortening of their length. This shortening, which follows the geometrical deformation of the lattice mesh being expanded in the transverse direction of the cylinder and reduced in the direction of its length, has the effect of making the accurate implantation of the device at its desired location very difficult.

The structure of an open weave, stainless steel wire results in loose wires at the ends of the cylinder which can be traumatizing to the arterial tissue and can result in a fibrous change therein and the formation of an intraluminal scar which can be the beginning of another stenosis.

The invention has the purpose of eliminating these inconveniences, particularly to provide a stent which can be easily and accurately placed in the desired arterial location with considerably less trauma than the prior art devices.

SUMMARY OF THE INVENTION

The intravascular endoprosthesis or stent according to this invention is characterized by the fact that it consists of a flat rectangular sheet intended to be rolled up into a spiral of small diameter around the catheter and held in the small diameter rolled-up state by a temporary holding means. It is then expanded to a greater diameter by unrolling, after the temporary holding means has been eliminated.

In this manner, the transition from the wound-up condition with a relatively small diameter to the unwound, expanded form of large diameter takes place without a reduction in the length of the endoprosthesis or stent because this dimensional change is obtained by unrolling rather than by dimensional deformation of its wall. This results in its implantation being simple and considerably more exact in the desired area.

Therefore, the use of a woven metal wire structure is no longer necessary to obtain the expansion and/or reduction of diameter of the stent and this allows for the possible use of a plain sheet for special applications.

However, when an open reticulated structure is required, it is still possible to provide the flat sheet forming the stent with apertures arranged to give it the appearance of a lattice with regular non-deformable links.

In both cases, whether plain or perforated sheet is used, the surface of the stent wall is smooth and the ends of the sheet are free of metal fibers which result in it being implanted with little or no trauma to the blood vessel. Additionally, the flat inner surface of the stent makes for a smooth flow of the fluid.

These effects comply simply and reliably with the requirements set.

The advantages provided by this invention will be shown more clearly in the following detailed description, especially concerning the potential use of non-thrombogenic and degradable materials instead of stainless steel.

BRIEF DESCRIPTION OF THE DRAWINGS

The enclosed exemplary drawings show one embodiment of the invention and one structural variation thereof.

FIG. 1a is a schematic perspective view of a stent in a wound-up state embodying features of the invention;

FIG. 1b is a perspective view of the stent shown in FIG. 1a in an unwound, expanded state;

FIG. 2 is a transverse cross section of the embodiment shown in FIG. 1a;

FIG. 3 is a transverse cross section of the embodiment shown in FIG. 1a in an expanded condition;

FIG. 4 is a partial plan view of a structural detail of the wall of the stent shown in FIGS. 1-3; and FIG. 5 is a partial view of structural details of a variation in the wall of the stent.

DETAILED DESCRIPTION OF THE INVENTION

The stent shown in FIGS. 1 to 4 consists of a flat rectangular sheet of biocompatible, malleable material, temporarily rolled up to form a cylinder 1 as shown in FIG. 1.

This rolled sheet 1 has an array of apertures which give it the appearance of a lattice 2 with non-deformable square links, the two parallel sides 3 of which are oriented in the longitudinal direction of the thus-formed cylinder. One angle of the reticulated structure is detailed in FIG. 4.

The covered edge 4 of the rolled sheet 1 is provided with holding flaps or fingers 5 which project outwardly from the longitudinal axis of the finished cylinder in order to engage links 2 of the latticework overlapping them.

In the embodiment shown, flaps 5 are spaced two by two within links 2 in order to facilitate their engagement in the latter.

In the left side of FIG. 1 and according to its section shown rolled up into a spiral having a relatively small diameter (d) over a deflated angioplasty balloon 6 which is mounted on the leading end of catheter 7; the two latter elements, the balloon and the catheter, being those commonly used for implantation of a stent.

The means to temporarily hold the stent in its rolled-up state is a holding wire 8 which is laced through the links of the last two layers of the spiral formed by the rolled sheet 1, close to the outer overlapping edge 9. The wire 8 is designed so that it can be removed by pulling from the outside.

In FIG. 1b, and according to its section shown in FIG. 3, the stent is shown in the expanded state with a larger diameter (D). It is expanded by inflating angioplasty balloon 6 after pulling out the holding wire. For the sake of clarity, balloon 6 and catheter 7 are not shown in FIG. 1b.

During inflation of the angioplasty balloon 6, the holding flaps 5 which are inclined in the direction opposite to that in which sheet 1 is unrolling, slide from link to link without engaging the latter.

When the angioplasty balloon 6 is deflated, the pressure of the blood vessel surrounding the stent has a tendency to re-roll the sheet 1 from which it is made. However, upon contraction of the sheet, holding flaps 5 which point in the direction of this re-rolling engage the first links of the lattice they encounter, hooking themselves into the edges of the latter, as can be seen in FIGS. 1b and 3. The stent is thus held firmly and cleanly without trauma in its expanded state in the vessel.

Of course, the rollable width of sheet 1 and the size of the lattice links are a function of the maximum diameter to which the angioplasty balloon 6 can be inflated and should be calculated so that after the maximum inflation of the balloon, edge 4 bearing flaps 5 is still overlapped by at least the last row of links of the opposite overlapping edge 9.

The design of the stent in a rolled sheet as described presents the advantage that it can easily be unrolled and rolled up on the angioplasty balloon 6 without modifying the latter.

The square form of links 2 of the lattice provides great radial stability of the cylinder, and that is of interest for the treatment of straight-line vessels. But the square form is not limitative.

Thus, for example, in order to facilitate the introduction of the endoprosthesis into an injured blood vessel, relatively high flexibility can be obtained with diamond-shaped links, such as links 10 of the variation shown in FIG. 5. In this alternative embodiment, the small axis (a) of the diamond-shaped links point in the longitudinal direction of the cylinder.

The holding flaps intended to oppose the re-rolling tendencies of the stent under the pressure of the vessel after the angioplasty balloon 6 has been deflated are raised extensions 11 of the sharp angles of links 10 on the covered edge 4 of the sheet. The raised extensions 11 hook into the corresponding inner angles of the links which overlap them.

The holes which provide the rolled sheet 1 with a lattice-like or reticulated structure can have any desired geometrical shape, depending on the particular effect sought and the mode of application of the stent, without eliminating the lattice-like appearance. The principle of expansion by unrolling provides the advantage of preventing any shortening of the stent, whatever the shape of the apertures.

The drawing shows the favorable effect already indicated, as compared to the present state of the art, with an absence of free traumatizing wires at the ends of the stent cylinder, the latter presenting only geometrical elements, squares under 2 and diamonds under 10, the same effect being shared by all other shapes.

The system for holding the stent in its expanded state with a large diameter (D), which is effected by the self-locking holding flaps 5 and 11, eliminates the requirement for material with good elastic characteristics. This allows for the advantageous use of malleable and non-thrombogenic materials and eventually resorbable materials.

The holding system of the invention can also be used with a plain rolled sheet requiring only that perforations be provided for the flaps to engage in the overlapping edge of the sheet.

It is also possible to design a stent without overlapping the two longitudinal edges of the cylinder by providing gripping elements on both of the longitudinal edges which implant themselves in the wall of the vessel itself under the pressure of the latter.

Another advantage of this invention is that it permits the use of a stent formed of all kinds of materials such as metals and synthetic and ceramic materials, provided they are biocompatible.

The use of synthetic materials allows for a wider choice of a coating formed of compatible products or materials which prevent cell proliferation inside the stent.

In the case of a material having very good elastic characteristics it is possible to shape the cylindrical sheet 1 so that its expansion by unrolling is obtained by its own elasticity. The final shape of the expanded device has the appearance of an open cylinder.

Upon implantation, the elasticity of the material thus opposes itself to the pressure of the vessel until the two forces are in balance. In this embodiment, there is no need for means such as flaps 5 or 11.

Finally, other temporary means for holding the wound-up stent around the catheter can be used; for example, a cuff or points of degradable adhesive or a combination of adhesive points and wire 8 which detaches said points when it is pulled out.

While specific embodiments of the invention have been described in detail, it will be appreciated by those skilled in the art that various modifications to the structure and use of the disclosed invention may be made in light of the overall teachings of the disclosure, without departing from the scope of the invention as defined by the appended claims.

What is claimed is:

1. An elongated cylindrically shaped intravascular stent assembly, comprising:
   a) a rectangularly shaped sheet which is in a rolled-up state with overlapping inner and outer longitudinal sections;
   b) means to expand the rolled-up sheet from a first rolled-up state with a first relatively small diameter;
   c) means to expand the rolled-up sheet to a second rolled-up state with a second relatively large diameter by unrolling the sheet;
   d) outwardly projecting fingers extending from the inner overlapping longitudinal section of the sheet; and
   e) openings in the outer overlapping longitudinal section of the sheet which are adapted to receive the projecting fingers which extend outwardly from the inner overlapping longitudinal section thereby locking the rolled-up longitudinal section thereby locking the rolled-up sheet in the second rolled-up state, said outwardly projecting fingers engaging with a select number of said openings to permit the selective radial expansion and locking of the tubular prosthesis in at least one fixed diameter.

2. The stent according to claim 1 characterized by the fact that said sheet is formed of elastic material and that its expansion by unrolling is caused by its own elasticity.

3. The stent according to claim 1 characterized by the fact that the sheet is made of malleable material and that the means to expand the stent is an angioplasty balloon disposed within an interior of the stent in its first rolled-up state which is adapted to be inflated to thereby expand the stent to its second rolled-up state.

4. The stent according to claim 1 characterized by the fact that the sheet of which it consists has been equipped with holes so arranged as to give it a reticulated, lattice-like appearance with undeformable regular links.

5. The stent according to claim 4 characterized by the fact that the links forming the rolled sheet are square-shaped and two parallel sides thereof are oriented in the longitudinal direction of the stent.

6. The stent according to claim 1 characterized by the fact that means to temporarily hold the stent in the rolled-up state around a catheter consists of a wire laced through the openings of at least two layers of sheet rolled upon itself, said wire being designed to be removed from outside the stent.

7. A method of delivering an expandable stent assembly to a desired location within a patient's blood vessel comprising:
   a) providing an elongated cylindrically shaped intravascular stent having
   a rectangularly shaped sheet which is in a rolled-up state with overlapping inner and outer longitudinal sections in a first rolled-up state with a relatively small diameter,
   outwardly projecting fingers extending from the inner overlapping longitudinal section, and
   openings in the outer overlapping longitudinal section which are adapted to receive the outwardly projecting fingers which extend from the inner overlapping longitudinal section to thereby lock the rolled-up sheet in a rolled-up state;
   b) providing an intravascular catheter having an expandable member on a distal portion thereof;
   c) mounting the stent in the first rolled-up state onto the expandable member;
   d) advancing the catheter within a patient's vascular system until the expandable member with the stent mounted thereon is located at a desirable site within a blood vessel;
   e) expanding the expandable member to expand the stent from the first rolled-up state to a second rolled-up state with a diameter larger than the diameter thereof in the first rolled-up state;
   f) constricting the expandable member to allow the fingers from the inner overlapping longitudinal section to be received by the openings provided in the outer overlapping longitudinal section to thereby lock the stent in the second rolled-up state, said outwardly projecting fingers engaging with a select number of said openings to permit the selective radial expansion and locking of the tubular prosthesis in at least one fixed diameter; and
   g) removing the catheter and expandable member thereon from a patient's vascular system.

8. The method of claim 6 wherein the expandable member is an angioplasty balloon.

9. An elongated cylindrically shaped stent, comprising:
   a) a rectangularly shaped sheet which is in a rolled-up state with overlapping inner and outer longitudinal sections;
   b) outwardly projecting fingers extending from the inner overlapping longitudinal section of the sheet; and
   c) openings in the outer overlapping longitudinal section of the sheet which are adapted to receive the projecting fingers extending outwardly from the inner overlapping longitudinal section which facilitate locking the rolled-up sheet in a rolled-up state, said outwardly projecting fingers engaging with a select number of said openings to permit the selective radial expansion and locking of the tubular prosthesis in at least one fixed diameter.

10. The stent of claim 9 wherein the sheet has a lattice-like structure.

11. The stent of claim 9 wherein the inner overlapping longitudinal section has a longitudinal edge with a plurality of fingers positioned along said edge which projects outwardly therefrom.

* * * * *

UNITED STATES PATENT AND TRADEMARK OFFICE
CERTIFICATE OF CORRECTION

PATENT NO. : 5,443,500
DATED : August 22, 1995
INVENTOR(S) : Ulrich Sigwart

It is certified that error appears in the above-indentified patent and that said Letters Patent is hereby corrected as shown below:

Claim 8, Column 6, line 35, change "6" to read --7--.

Signed and Sealed this

Twenty-sixth Day of March, 1996

Attest:

BRUCE LEHMAN

Attesting Officer     Commissioner of Patents and Trademarks